United States Patent [19]

Travers et al.

[11] Patent Number: 5,321,195
[45] Date of Patent: Jun. 14, 1994

[54] PROCESS FOR THE ISOMERIZATION OF OLEFINS

[75] Inventors: Christine Travers, Rueil Malmaison; Jean-Pierre Burzynsky, Sainte Foy Les Lyons; Jean Dagand, Paris; Philippe Courty, Houilles, all of France

[73] Assignee: Institut Francais Du Petrole, Rueil Malmaison, France

[21] Appl. No.: 13,599

[22] Filed: Feb. 4, 1993

[30] Foreign Application Priority Data

Sep. 15, 1992 [FR] France .................... 92 10949

[51] Int. Cl.$^5$ ............................................. C07C 5/27
[52] U.S. Cl. ................................................. 585/671
[58] Field of Search ......................... 585/664, 666, 671

[56] References Cited

U.S. PATENT DOCUMENTS 4,038,337 7/1977 Manara et al. .................... 585/671
4,436,949 3/1984 Myers et al. ........................ 585/664

FOREIGN PATENT DOCUMENTS 279954 3/1962 Australia .
58-024350 2/1983 Japan .

Primary Examiner—Asok Pal
Assistant Examiner—P. Achutamurthy
Attorney, Agent, or Firm—Millen, White, Zelano & Branigan

[57] ABSTRACT

A process for the skeletal isomerization of n-olefins containing at most 20 carbon atoms, comprising bringing a charge containing olefins into contact with a catalyst based on alumina which is impregnated with a clearly determined amount of $TuO_2$, and subjected to a steam treatment. The process is carried into effect in the presence of steam.

15 Claims, No Drawings

PROCESS FOR THE ISOMERIZATION OF OLEFINS

The present invention describes a process for the isomerization of olefins having at most 20 carbon atoms and more particularly for the isomerization of n-butenes to isobutenes and n-pentenes to isopentenes (iso-anylenes), using a particular catalyst.

BACKGROUND OF THE INVENTION

The reduction of lead alkyls in petrols has caused refiners for many years now to envisage incorporating different compounds and in particular alcohols and esters into petrol, to permit an increase in the octane number. Besides methanol which is one of the most attractive known additives, MTBE (methyl-tertiobutyl ether) has anti-knock properties which permit an improvement in the quality of the petrols and an increase in their octane number, such increase being greater than that which is obtained with methanol. MTBE also has many other advantages such as:

a boiling point corresponding to that of the components of the petrol which have the lowest anti-knock properties,
a vapor pressure which is compatible with the above-mentioned components,
an excellent freezing point,
low solubility in water,
complete miscibility with hydrocarbons, etc.

MTBE is generally produced from isobutene and methanol in accordance with the following reaction:

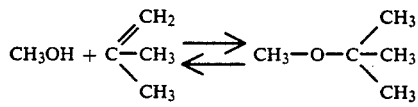

Isobutene is generally contained in $C_3$-$C_4$ olefinic cuts obtained from the effluents from catalytic cracking, steam cracking, thermal cracking and visbreaking. However the amounts of isobutene provided by those different processes are not sufficient to permit a broad development of the MTBE production process.

It is for that reason that, in order to produce larger amounts of isobutene, it has been proposed that the butenes contained in the effluents from the above-mentioned processes are to be completely or almost completely isomerized to provide isobutenes.

Many processes associated with many catalysts have been proposed in the literature. The catalysts used are generally based on alumina or more particularly aluminas which have been activated or treated with vapor (U.S. Pat. No. 3,558,733), whether involving alumina h or g, halogenated aluminas (U.S. Pat. No 2,417,647) bauxite, aluminas treated with derivatives of boron, silicon (U.S. Pat. No. 4,013,590, U.S. Pat. No 4,038,337 GB 2 129 701 and U.S. Pat. No 4,434,315) or zirconium and various silica-aluminas, etc.

Most of those catalysts exhibit a relatively low level of conversion per pass and a low degree of selectivity due to the parasitic reactions such as cracking and polymerization, which latter also give rise to a rapid drop-off in the levels of performance.

SUMMARY OF THE INVENTION

The present invention lies in using a catalyst which makes it possible to achieve improved levels of performance, in particular in regard to the degree of selectivity, and which affords enhanced stability.

It has been found that a catalyst obtained from alumina and preferably eta or gamma alumina to which a clearly defined amount of titanium (from 0.03 to 0.6% by weight) has been added and which has preferably been subjected to a steam treatment under precise conditions surprisingly resulted in very markedly improved levels of selectivity, levels of conversion and cycle time.

In the process according to the invention it is possible to isomerize either a $C_4$ olefinic cut alone resulting from the above-mentioned processes, after the $C_3$ cut has been removed, or the whole of the $C_3$-$C_4$ olefinic cut.

In accordance with the invention straight chain olefinic hydrocarbons containing from 5 to 20 carbon atoms per molecule can also be isomerized.

The charge to be isomerized is brought into contact with the catalyst at a temperature of between 300° C. and 570° C. (preferably between 400° and 550° C. when the charge is formed by butenes and/or pentenes) at a pressure of between 1 and 10 bars absolute (and preferably between 1 and 5 bars absolute when the charge is formed by butenes and/or pentenes).

The space velocity is between 0.1 and 10 $h^{-1}$ expressed in terms of volume of olefinic charge per volume of catalyst and per hour (and preferably between 0.5 and 6 $h^{-1}$ when the charge is formed by butenes and/or pentenes).

According to the invention the process is carried out in the presence of water in order to minimize the undesirable secondary reactions. The amount of water introduced into the reactor is such that the $H_2O$/olefinic hydrocarbons molar ratio is between 0.1 and 10 (and preferably between 0.5 and 3 when the charge is formed by butenes and/or pentenes).

For preparation of the catalyst, it is possible to use commercial aluminas, preferably activated, which are selected preferably from the group of eta and gamma aluminas, having a low proportion of alkali metals, for example containing less than 0.1% of sodium.

The specific surface area of the alumina will advantageously be between 10 and 500 $m^2/g$ and preferably between 50 and 450 $m^2/g$, its pore volume being between 0.4 and 0.8 $cm^3/g$.

The catalysts according to the invention are prepared by adding from 0.05 to 1% and preferably from 0.085 to 0.5% of titanium dioxide to the alumina carrier. Any process which permits the addition of that titanium dioxide can be used. It is possible for example to dissolve a compound of titanium in the solution containing the aluminum compound and to adjust the conditions of precipitation of the alumina in order for titanium hydroxide to co-precipitate. It is also possible to add to aluminum hydroxide in gel form (aluminium a-trihydrate, b-trihydrate or a-monohydrate) at least one compound of titainium selected from the group formed by titanium dioxide in the futile and anatase forms, the sub-oxides TiO and $Ti_2O_3$, titanic acids, alkali metal, alkaline-earth metal and ammonium titanates and soluble and insoluble, organic and inorganic titanium salts.

It is also possible to take as the starting point a shaped alumina carrier and to impregnate it with a solution of an organic or inorganic titanium salt; generally the addition of titanium can be effected prior to, in the course of or after the operation of shaping the catalyst carrier.

A preferred process comprises adding to an organic solution (for example an alcohol solution) of at least one organic compound of aluminium (for example an alkoxyaluminium such as aluminium isopropylate), at least one organic compound of titanium, for example tetraethoxytitanium and then hydrolyzing the solution obtained in that way.

It is also possible to add the titanium in the form of an easily hydrolyzable inorganic compound such as titanium tetrachloride $TiCl_4$.

Another preferred process comprises adding controlled amounts of an organic compound based on titanium, for example an alkoxy titanium such as tetraethyltitanium and/or an inorganic compound of titanium (for example titanium trichloride) in the course of the ZIEGLER synthesis of polyalkoxyaluminium, by the reaction of an alkylaluminium (for example triethylalunlinium), ethylene and at least one of said compounds of titanium. By polymerization and then subsequent oxidation, the above-mentioned polyalkoxyaluminium is prepared, the hydrolysis of which will result in polyols and aluminium hydroxide containing titanium.

It has been found in experiments that those processes resulted in a particularly high degree of dispersion of the titanium ions in the alumina matrix as is obtained after hydrolysis of the alkoxyaluminium or the polyalkoxyaluminium. For example, when the carrier is in the form of balls or extrudates, etc . . . , the preferred processes for the impregnation of titanium make it possible to achieve a content of $TiO_2$ which is constant from one ball to another or from one extrudate to another; if the desired mean concentration is C%, the concentration C, from one ball to another or from one extrudate to another, with the preferred methods of the invention, will remain between C±5% of that concentration and even between ±3% by weight. Still better results were obtained by using catalyst carriers which contain more particularly from 0.06 to 0.15% of $TiO_2$.

The titanium content on the catalyst is measured by X-ray fluoresence.

The catalyst obtained in that way is then dried at a temperature of between 100° and 130° C. and possibly calcined in air at a temperature of between 400° and 800° C. and preferably between 450° and 750° C. for periods of time varying from 1 to 5 hours. It can then advantageously be treated in steam at a temperature of between 120° and 700° C. and preferably between 300° and 700° C. under a steam partial pressure of higher than 0.5 bars and preferably between 0.6 and 1 bar for a period of time of from 0.5 to 120 hours and preferably from 1 hour to 100 hours.

The levels of performance in the isomerization operation will be expressed by:

1) conversion of butenes $$C = \frac{S(\% \text{ n-butenes})\text{charge} - S(\% \text{ n-butenes})\text{effluent}}{S(\% \text{ n-butenes})\text{charge}} \times 100$$

2) selectivity in respect of isobutenes $$S = \frac{(\% \text{ isobutene})\text{effluent} - (\% \text{ isobutene})\text{charge}}{S(\% \text{ n-butenes})\text{charge} - S(\% \text{ n-butenes effluent})} \times 100$$

3) yield in respect of isobutene $$R = C \times S/100.$$

The following Examples set out the invention in greater detail without limiting the scope thereof.

EXAMPLE 1

Catalyst A not in accordance with the invention

A commercial alumina g carrier of a surface area of 200 $m^2/g$ is subjected to a steam treatment at 560° C. for a period of 20 hours at a steam partial pressure equal to 0.8 bars. That catalyst is used in isomerization of a $C_4$ olefinic cut whose composition is set out in Table 1. The operating conditions are as follows:

LHSV=2 $h^{-1}$
$H_2O/C_4$=(mole)=2
T=530° C.
p=1 bar absolute

The levels of performance obtained are shown in Table 1 after 1 hour of operation and in Table II after 30 hours of operation.

It can be seen that the levels of performance are low and that they fall in the course of time.

EXAMPLE 2

Catalyst B according to the invention

The commercial alumina g carrier used in Example 1 is impregnated with 0.1% of titanium from decahydrated titanium oxalate in aqueous solution, then dried at 100° C. for a period of 2 hours and calcined at 600° C. for a period of 2 hours. The catalyst B obtained in that way is subjected to a steam treatment equivalent to that described in Example 1 and then used in the process for the isomerization of a $C_4$ olefinic cut under the operating conditions described above.

The levels of performance obtained are shown in Table I after 1 hour of operation and in Table II after 30 hours of operation.

The levels of performance obtained with catalyst B according to the invention are markedly superior to those obtained with catalyst A which is not in accordance with the invention, in regard to activity, selectivity and stability.

EXAMPLE 3

Catalyst C according to the invention

Catalyst C differs from catalyst B in that it is not subjected to a steam treatment after the deposit of titanium, drying and calcination which are effected under the operating conditions described in Example 2.

The catalyst C is used in the process for the isomerization of a $C_4$ olefinic cut under the operating conditions described above.

The levels of performance obtained with catalyst C are shown in Table I after 1 hour of operation and Table II after 30 hours of operation.

It is observed that the levels of performance of the catalyst C are between those of the catalysts A and B.

In Table I, $C_2$ designates ethane, $C_2=$: ethylene, $C_3$: propane, $iC_4$: isobutane, $nC_4$: n-butane, $C_4=2TR$: trans-but-2-ene, $C_4=1$: but-1-ene, $iC_4==$:isobutene, $C_4=2Cis$: cis-but-2-ene, $C_4==$: butadiene and $C_5+$: hydrocarbons with more than 5 carbon athens.

TABLE I

| | Charge | Catalyst A | Catalyst B | Catalyst C |
|---|---|---|---|---|
| $H_2O/C_4=$ (mole) | — | 2 | 2 | 2 |
| LHSV ($h^{-1}$) | — | 2 | 2 | 2 |
| Operating time (h) | — | 1 | 1 | 1 |
| $CH_4$ | 0 | 0.052 | 0.06 | 0.03 |
| $C_2$ | 0 | 0.016 | 0.018 | 0.01 |

TABLE I-continued

| | | | | |
|---|---|---|---|---|
| $C_2=$ | 0 | 0.126 | 0.315 | 0.12 |
| $C_3$ | 0 | 0.005 | 0 | 0 |
| $C_3=$ | 0 | 1.228 | 2.571 | 1.52 |
| $iC_4$ | 0.216 | 0.28 | 0.292 | 0.29 |
| $nC_4$ | 21.76 | 21.537 | 21.545 | 21.55 |
| $C_4=2TR$ | 2.732 | 22.44 | 18.5 | 21.1 |
| $C_4=1$ | 63.878 | 16.37 | 14.8 | 15.3 |
| $iC_4=$ | 5.617 | 19.11 | 25.73 | 22.13 |
| $C_4=2Cis$ | 5.139 | 17.38 | 14.25 | 16.35 |
| $C_4==$ | 0.03 | 0.088 | 0.07 | 0.08 |
| $C_5+$ | 0.628 | 1.368 | 1.85 | 1.52 |
| Conversion % | — | 22.25 | 33.7 | 26.5 |
| Selectivity % | — | 83.7 | 83.1 | 86.8 |
| Yield % | — | 18.6 | 28.0 | 23.0 |

TABLE II

| | Catalyst A | Catalyst B | Catalyst C |
|---|---|---|---|
| $H_2O/C_4=$ (mole) | 2 | 2 | 2 |
| LHSV ($h^{-1}$) | 2 | 2 | 2 |
| Operating time (h) | 30 | 30 | 30 |
| Conversion (%) | 21.0 | 33.45 | 25.5 |
| Selectivity (%) | 86.0 | 83.5 | 87.5 |
| Yield (%) | 18.05 | 27.9 | 22.0 |

We claim:

1. A process for the isomerization of straight-chain olefinic hydrocarbons having at most 20 carbon atoms per molecule to branched-chain molecules, comprising contacting said hydrocarbons with a catalyst consisting essentially of alumina and having disposed therein 0.03% to 0.6% by weight of $TiO_2$, at a temperature of between 300° C. and 570° C., a pressure of between 0.1 and 1 MPa, at a space velocity of between 0.1 and 10 $h^{-1}$, and in the presence of injected water, the injected water/olefinic hydrocarbons molar ratio being between 0.1 and 10.

2. A process according to claim 1 wherein said catalyst is subjected to a steam treatment before being brought into contact with the hydrocarbons, said treatment taking place at between 120° and 700° C. under a steam partial pressure of higher than 0.5 bars for a period of time of from 0.5 to 120 hours.

3. A process according to claim 1, wherein the straight chain olefinic hydrocarbons treated are selected from the group consisting of butenes and pentenes.

4. A process according to claim 1, wherein the isomerization temperature is between 400° and 550° C.

5. A process according to claim 1, wherein the isomerization pressure is between 0.1 and 0.5 MPa.

6. A process according to claim 1, wherein the space velocity is between 0.5 and 6 $h^{-1}$.

7. A process according to claim 3, wherein the injected water/hydrocarbons molar ratio is between 0.5 and 3.

8. A process according to claim 1, wherein the alumina is a gamma alumina.

9. A process according to claim 2, wherein the alumina is an eta alumina.

10. A process according to claim 1, wherein the amount of sodium in the alumina is less than 0.1% by weight.

11. A process according to claim 1, wherein the specific surface area of the alumina is between 10 and 550 $m^2/g$.

12. A process according to claim 1, wherein the pore volume of the alumina is between 0.4 and 0.8 $cm^3/g$.

13. A process according to claim 2, wherein the steam treatment takes place at a temperature of from 300° to 700° C.

14. A process according to claim 2, wherein the steam treatment takes place at a steam partial pressure of between 0.6 and 1 bar.

15. A process according to claim 1, wherein alumina and $TiO_2$ are the only components in the catalyst.

* * * * *

UNITED STATES PATENT AND TRADEMARK OFFICE
CERTIFICATE OF CORRECTION

PATENT NO. : 5,321,195
DATED : June 14, 1994
INVENTOR(S) : Christine TRAVERS et al.

It is certified that error appears in the above-indentified patent and that said Letters Patent is hereby corrected as shown below:

Claim 9, Column 6, Line 20: After claim delete "2" and insert --1--.

Signed and Sealed this

Sixth Day of December, 1994

Attest:

BRUCE LEHMAN

Attesting Officer     Commissioner of Patents and Trademarks